United States Patent
Rousselot et al.

(10) Patent No.: US 11,224,218 B2
(45) Date of Patent: Jan. 18, 2022

(54) HEAMOGLOBIN AND USES THEREOF

(75) Inventors: Morgane Rousselot, Plouenan (FR); Delphine Dutheil, Saint Pol de Leon (FR); Franck Zal, Morlaix (FR)

(73) Assignee: HEMARINA, Morlaix (FR)

( * ) Notice: Subject to any disclaimer, the term of this patent is extended or adjusted under 35 U.S.C. 154(b) by 58 days.

(21) Appl. No.: 13/318,860

(22) PCT Filed: May 7, 2010

(86) PCT No.: PCT/EP2010/056299
§ 371 (c)(1),
(2), (4) Date: Nov. 4, 2011

(87) PCT Pub. No.: WO2010/128159
PCT Pub. Date: Nov. 11, 2010

(65) Prior Publication Data
US 2012/0052136 A1 Mar. 1, 2012

Related U.S. Application Data

(60) Provisional application No. 61/176,271, filed on May 7, 2009.

(30) Foreign Application Priority Data

May 7, 2009 (EP) .................................. 09305415

(51) Int. Cl.
| C07K 14/435 | (2006.01) |
| C12N 5/02 | (2006.01) |
| A01N 1/02 | (2006.01) |
| A61K 38/00 | (2006.01) |
| C12N 5/00 | (2006.01) |

(52) U.S. Cl.
CPC ...... *A01N 1/0226* (2013.01); *C07K 14/43536* (2013.01); *C12N 5/0018* (2013.01); *A61K 38/00* (2013.01); *C12N 2501/998* (2013.01)

(58) Field of Classification Search
None
See application file for complete search history.

(56) References Cited

U.S. PATENT DOCUMENTS

| 5,405,742 A * | 4/1995 | Taylor .................... A01N 1/02 435/1.2 |
| 5,631,219 A * | 5/1997 | Rosenthal et al. .......... 424/85.2 |
| 7,220,538 B2 * | 5/2007 | Fischer et al. ............. 435/1.1 |
| 2003/0181358 A1 | 9/2003 | Zal et al. |
| 2008/0227136 A1 * | 9/2008 | Pla et al. ..................... 435/29 |
| 2010/0209902 A1 | 8/2010 | Zal et al. |
| 2012/0040453 A1 * | 2/2012 | Zal .............................. 435/325 |

FOREIGN PATENT DOCUMENTS

| DE | 10220990 A1 | 11/2003 | |
| EP | 0784983 A2 * | 7/1997 | ............. A61K 31/00 |
| WO | WO 9527041 A1 * | 10/1995 | ........... C12N 5/0018 |
| WO | 2009050343 A | 4/2009 | |

OTHER PUBLICATIONS

Padlan, E.A., et al. 1968 Nature 220: 376-378.*
Hirsch, R.E., et al. 1997 Art. Cells, Blood Subs., and Immob. Biotech. 25(5): 429-444.*
NCBI taxonomy browser (hediste diversicolor), retrieved from the internet Jun. 22, 2015: 2 pages total.*
Rousselot, M., et al. 2006 The FEBS Journal 273: 1582-1596.*
Hesselberg, T. 2007 Naturwissenschaften 94: 613-621. (Year: 2007).*
Economides A P et al: "The respiratory function of the blood of Neanthes (=Nereis) virens (Bars) (Polychaeta: Nereidae)", Comparative Biochemistry and Physiology 1975, vol. 51, No. 1 A, 1975, pp. 219-223, XP023590958.
Suzuki T et al: "The giant extracellular hemoglobin from the polychaete Neanthes diversicolor. The cDNA-derived amino acid sequence of linker chain L2 and the exon/intron boundary conserved in linker genes", Biochimica et Biophysica Acta—Gene Structure and Expression 1994 NL, vol. 1217, No. 3, 1994, pp. 291-296, XP023469023.
Christine Chabasse et al: "Gene Structure and Molecular Phylogeny of the Linker Chains from the Giant Annelid Hexagonal Bilayer Hemoglobins", Journal of Molecular Evolution, Springer-Verlag, NE, vol. 63, No. 3, Jul. 12, 2006 (Jul. 12, 2006), pp. 365-374, XP019441462.
Waxman L: "The Structure of Annelid and Mollusk Hemo Globins", Journal of Biological Chemistry, vol. 250, No. 10, 1975, pp. 3790-3795, XP002539399.
Rousselot Morgane et al: "Arenicola marina extracellular hemoglobin: a new promising blood substitute", Biotechnology Journal, Wiley-VCH Verlag, Weinheim, DE, vol. 1, No. 3, Jan. 1, 2006 (Jan. 1, 2006), pp. 333-345, XP002480915.
International Search Report, dated Aug. 2, 2011, in Application No. PCT/EP2010/056299.
J Mol Biol. Jan. 12, 1996;255(1):154-69. Martin PD1, Kuchumov AR, Green BN, Oliver RW, Braswell EH, Wall JS, Vinogradov SN; Mass Spectrometric Composition and Molecular Mass of Lumbricus Terrestris Hemoglobin: A Refined Model of its Quaternary Structure; Biochemistry Department School of Medicine, Wayne State University, Detroit, MI 48201, USA; Jan. 12, 1996;255(1):154-69.

* cited by examiner

*Primary Examiner* — Marsha Tsay
(74) *Attorney, Agent, or Firm* — Nixon & Vanderhye

(57) ABSTRACT

The present invention relates to isolated haemoglobin from worms belonging to the Nereididae family and its use in cell culture medium, in preservation solutions and as artificial oxygen carrier for transfusion.

15 Claims, 9 Drawing Sheets
(5 of 9 Drawing Sheet(s) Filed in Color)

HEAMOGLOBIN AND USES THEREOF

FIELD OF THE INVENTION

The invention relates to a novel isolated haemoglobin that can serve for cell culture, organ preservation solution and blood substitute.

BACKGROUND OF THE INVENTION

The present invention relates to haemoglobin and its property to fix, carry and release oxygen in a simple partial pressure of oxygen. One particular interest of such haemoglobin is its use as oxygen carrier for industrial and therapeutic applications. Two viable categories of oxygen therapeutics currently exist: haemoglobin-based oxygen carriers (HBOCs) and perfluorocarbons (PFCs). Haemoglobin taken directly from red blood cells can not be used as an intravascular oxygen carrier. To avoid spontaneous breakdown of haemoglobin and the toxicity of haemoglobin extracted from red blood cells, haemoglobin-based oxygen carriers use purified human (Riess et al. Chem Rev 2001, 101:2797), animal (bovine) (Lok et al Nature 2001, 410:855) or recombinant (Looker et al Nature 1992, 356:258) haemoglobin as raw materials. Each chain of purified haemoglobin is then covalently bridged with other globin chains or microencapsulated. Perfluorocarbons are liquid fluorinated hydrocarbon compounds capable of dissolving large amounts of oxygen and then delivering this oxygen. However, in this case the oxygen partial pressure needs to be higher than air oxygen partial pressure.

Oxygen therapeutics have been developed for two major purposes: i) they can function as alternatives to blood transfusion in order to avoid, reduce or delay transfusion of allogenic blood and ii) improvement of tissue oxygenation of organs with poor blood supply.

The inventors have previously shown that the extracellular polymeric haemoglobin of the polyachete annelid *Arenicola marina* can be used as an oxygen therapeutic (Rousselot et al 2006 Biotech Journal 1:333). Said haemoglobin is easily available and can be purified to a homogeneous product avoiding costly synthetic steps. It is also easy to store and is less likely to cause immunogenic responses as it is not glycosylated as already demonstrated. A model of quaternary structure of this extracellular haemoglobin from *Arenicola marina* has been proposed by Zal et al. (Zal et al. Eur. J. Biochem 1997, 243:85). The study indicated the existence of ten subunits: eight of which are globins, including two monomers (M=~15 kDa) and five disulfide bonded trimers (T=~49 kDa). The remaining two chains correspond to linker chains (L) that are disulfide bonded to form homo and hetero dimmers (~50 kDa). Three and six copies of each of the two monomers subunits and one copy of the trimer form a dodecamer subunit (D) with a mean mass close to 200 kDa. Twelve such complexes of globin chains are linked together by 42 linker chains to reach a total mass of 3648±24 kDa.

While studying another family of polychaete annelids, the inventors isolated a novel haemoglobin from the Nereididae family, that presents the advantage of being stable and functional for a longer period of time in several media. The worms belonging to the Nereididae family differ from those belonging to the Arenicolidae family for several aspects starting by their phylogeny. From a point of view of evolution, these two families have diverged from each other since several million years ago (Halanych and Janosik, 2006). Furthermore, these two annelid families do not have the same morphology, the same behavior, the same genes, the same physiology neither the same organism biology. For example, Nereididae are errant species compared to the *Arenicola* worms which live in sand gallery on the intertidal area. Furthermore, Arenicolidae reproduce several times during their lifespan whereas Nereididae reproduces once the year and dies after the reproduction period.

The inventors then found that this novel isolated haemoglobin from the Nereididae family can be used as oxygen carrier for several applications, in particular for cell culture media complement, as a supplement for organ preservation solution or in order to be used as an artificial oxygen carrier for transfusion.

SUMMARY OF THE INVENTION

One object of the invention is an isolated haemoglobin or a portion thereof from worms belonging to the family of Nereididae, having:
 a P50 from 5 to 15, preferably from 9 to 12 mm Hg at 6-7° C., from 12 to 20, preferably from 15 to 18 mm Hg at 16-17° C. and from 20 to 50, preferably from 30 to 44 mm Hg at 36-37° C.
 preferably no free cysteines,
 preferably no glycosylations.

In one embodiment of the invention, said haemoglobin is isolated from *Nereis virens*, also called *Nereis diversicola*, *Neanthes virens* or *Hediste diversicolor* (although these scientific names are different they concern the same species) or other terms synonyms of these species.

In another embodiment, said haemoglobin is in the form of an aqueous solution, a frozen solution, a thawed solution or a lyophilised powder.

Another object of the invention is a pouch comprising the haemoglobin as described above. The haemoglobin according to the invention may be used as a blood substitute. In this case, the haemoglobin is present in a physiologically acceptable medium. By "physiologically acceptable medium", it is meant a medium which is compatible with an in vivo injection into the blood of a living human. The physiologically acceptable medium is then compatible with the human blood, does not cause any adverse event and preserves the activity of the haemoglobin according to the invention. The blood substitute may be present in any container, such as a pouch, a bottle, a flask, a bag . . . . The haemoglobin may be in the form of an aqueous solution, a frozen solution, a thawed solution or a lyophilised powder.

Another object of the invention is a cell culture medium comprising the haemoglobin as described above.

In one embodiment, said cell culture medium is a medium suitable for bioproduction.

In another embodiment, said cell culture medium is a medium suitable for cell growth.

In another embodiment, the concentration of the haemoglobin in said cell culture medium is at least 0.050 g/l.

In another embodiment, the concentration of the haemoglobin in said cell culture medium is at least 1 g/l.

Another object of the invention is a preservation solution comprising the haemoglobin as described above.

In one embodiment, said preservation solution is Viaspan® or Custodiol®.

In another embodiment, the concentration of the haemoglobin in said preservation solution is at least 0.150 g/l.

Another object of the invention is an artificial oxygen carrier for transfusion comprising the haemoglobin as described here above.

DETAILED DESCRIPTION OF THE INVENTION

One object of the invention is an isolated haemoglobin or a portion thereof from worms belonging to the family of Nereididae (Annelid, Polychaete) having:
  a $P_{50}$ from 5 to 15, preferably from 9 to 12 mm Hg at 6-7° C., from 12 to 20, preferably from 15 to 18 mm Hg at 16-17° C. and from 20 to 50, preferably from 30 to 44 mm Hg at 36-37° C.
  preferably no free cysteines, and
  preferably no glycosylations.

In one embodiment of the invention, said haemoglobin is an extracellular haemoglobin, which refers to a haemoglobin not contained in a cell and dissolved in the blood.

In one embodiment of the invention, said haemoglobin is isolated from worms belonging to the genus *Nereis*.

In another embodiment, said haemoglobin is isolated from worms belonging to the specie *Nereis virens*, also called *Nereis diversicola, Neanthes virens* or *Hediste diversicolor*.

*Nereis* worms can be collected on the intertidal area or on the estuarine zone. Despite their vernacular worm name, clam worms are common in a variety of benthic habitats, including sandflats, mudflats, shellfish beds, and algal mats. Some species can also be found living among barnacles and encrusting algae (fouling communities) on man-made structures, such as pilings. *Nereis* are ubiquitous in distribution, common in marine and estuarine waters along the West, East, and Gulf Coasts in US and on most of European costs. Some species can be found in the intertidal zone among rocks or in mudflats and sandflats of higher salinity waters. It is also one of the major annelid species farms for aquaculture of fishs or shrimps in order to serve as a supplement food.

In one embodiment of the invention, said haemoglobin has a $P_{50}$ from 5 to 15, preferably from 9 to 12 mm Hg at 6-7° C., from 12 to 20, preferably 15 to 18 mm Hg at 16-17° C. and from 20 to 50, preferably 30 to 44 mm Hg at 36-37° C.

$P_{50}$ is a parameter used to measure the affinity of a respiratory pigment to oxygen, which corresponds to 50% oxygen saturation of the binding sites of a respiratory pigment. This corresponds to oxygen's efficiency in fixing to haem. $P_{50}$ can be measured using the hemox technique (Toulmond et al., 1990 Biol. Bull. 179: 366).

In another embodiment of the invention, said haemoglobin has a P50 of about 10.98 mm Hg at 6.65° C., of about 16.57 mm Hg at 16.51° C. and of about 37.11 mm Hg at 36.56° C., wherein said P50 is measured:
  according to a diffusion chamber operating as described in Paul R., et al, J. Comp. Physiol. 1997, 167B, 309-408 entitled *Circulation and respiratory control in millimetre-sized animals (Daphni magna, Folsomia candida) studied by optical methods;*
  in the following medium: 2.5 mM CaCl2, 145 mM NaCl, 0.2 mM MgCl2, 4 mM KCl, 10 mM Hepes, adjusted to pH 7.35 with NaOH;
  and the concentration of said haemoglobin in said medium being from 30 to 70 mg/ml, preferably from 40 to 60 mg/ml.

In one embodiment of the invention, said haemoglobin has a molecular weight from 3 to 4 million Daltons.

An object of the invention is also a portion of said haemoglobin. By "portion of said haemoglobin", it is meant a fragment of said haemoglobin which is able to fulfill the functions of the whole haemoglobin, and particularly oxygen carrying. Such portions are preferably selected from the group consisting of chains, dimers, trimers, linkers and dodecamers. Preferably, the molecular weight of said portion is comprised from 14 000 to 30 000 Daltons for chains and dimers; from 14 000 to 60 000 Daltons for trimers; from 14 000 to 250 000 Daltons for dodecamers; from 14 000 to 500 000 Daltons for didodecamers; and from 500 000 to 4 000 000 Daltons. The molecular weight can be measured by light diffusion under several angles (MALLS-Multi Angle Lazer Light Scattering).

In one embodiment of the invention, said haemoglobin comprises chains of polymerised globins: at least one monomer sub-unit and at least one trimer sub-unit. Preferably, the haemoglobin of the invention includes one or two monomers of 10 to 20 kDa each, more preferably of 15 to 16 kDa each, and one trimer of 40 to 55 KDa, preferably 48 to 50 kDa. The haemoglobin of the invention may also include a linker. In an embodiment, the linker has a molecular weight of 10 to 100 kDa, more preferably of 40 to 60 kDa. According to an embodiment, the linker is dimeric and composed of two monomeric chains around 20 to 30 kDa, preferably between 22 to 26 kDa.

Preferably, according to the invention, said haemoglobin has no free cysteins. Preferably, according to the invention, said haemoglobin has also no glycosylations. This decreases the risk of immunogenic responses.

In another embodiment of the invention, said haemoglobin has an $n_{50}$ from 1 to 2, preferably 1 to 1.3 at 6-7° C., from 1 to 2.5, preferably 1 to 1.3 at 16-17° C. and from 1 to 3, preferably 1 to 2 at 36-37° C. $n_{50}$ is the haemoglobin cooperativity coefficient and is defined as being the parameter used to estimate the oxygen binding facility to bind oxygen once on site is already bind by oxygen. $n_{50}$ can be calculated using the oxygen saturation curves of a respiratory pigment obtained using the hemox technique.

In another embodiment of the invention, said haemoglobin has an n50 of about 1.19 at 6.65° C., of about 1.17 at 16.51° C. and of about 1.47 at 36.56° C., wherein said $n_{50}$ is measured according to a diffusion chamber operating as described in (Paul R., et al, J. Comp. Physiol. 1997, 167B, 309-408).

In one embodiment of the invention, the haemoglobin as described here above is present in a composition in the form of an aqueous solution, a frozen solution, a thawed solution or a lyophilised powder.

In one embodiment, the haemoglobin of the invention is conserved in a storage buffer. Said storage buffer is an acceptable medium. It may comprise 0-2.5 mM CaCl2, 0-300 mM NaCl, 0-1 mM MgCl2, 0-5 mM KCl, 0-1M Hepes and/or Tris or any other buffer able to adjust the pH to the required value, adjusted to pH 7.0-7.8 with NaOH.

The invention also relates to an aqueous solution comprising the haemoglobin of the invention. In a preferred embodiment, the concentration of haemoglobin in the solution is of 0.050 to 200 mg/ml, more preferably 30 to 100 mg/ml, even more preferably 30 to 60 mg/ml.

In one embodiment of the invention, the solution comprising the haemoglobin as described here above is formulated to have a pH of from about 6-8, preferably from about 7.0-7.8.

Another object of the invention is also a pouch comprising the haemoglobin as described above.

In one embodiment, the haemoglobin of the invention is conserved in a storage buffer. Said storage buffer is a physiologically acceptable medium. It may comprise 0-2.5 mM CaCl2, 0-300 mM NaCl, 0-1 mM MgCl2, 0-5 mM KCl, 0-1M Hepes and/or Tris or any other buffer able to adjust the pH to the required value, adjusted to pH 7.0-7.8 with NaOH.

The inventors found that the haemoglobin of the invention is stable in medium, which is particularly suitable for cell culture medium. In addition, the inventors surprisingly found that the haemoglobin of the invention promotes cell growth, improves cell viability and greatly improves recombinant protein production. Optimizing a cell culture medium in order to obtain the greatest amount of protein and the most efficient means of productivity is one goal of recombinant protein production, as any improvement can have enormous benefits economically.

Another object of the invention is thus a culture medium comprising the haemoglobin as described above.

As used herein, the terms "culture medium", "cell culture medium" and "medium formulation" refer to a nutritive solution for the maintenance, growth, propagation, and/or expansion of cells in an artificial environment outside of a multicellular organism or tissue. Cell culture medium may be optimised for a specific culture use, including for example, cell growth culture medium formulated to promote cell growth or cell culture production medium formulated to promote recombinant protein production.

As used herein, a cell culture medium suitable for bioproduction refers to a cell culture medium formulated to promote recombinant protein production. Said recombinant protein may be any protein of interest, for example an antibody such as an anti-TNFalpha antibody, an anti-IL-12 antibody, an anti-IL-18 antibody or an anti-EPO receptor antibody.

Examples of culture mediums include, but are not limited to, Dulbecco's Modified Eagle's Medium (DMEM), DMEM/F12, Minimal Essential Medium (MEM), Basal Medium Eagle (BME), RPMI 1640, F-10, F-12, alpha-Minimal Essential Medium (alpha-MEM), Glasgow's Minimal Essential Medium (G-MEM), PF CHO (SAFC Biosciences), Ex-cell® 325 PF CHO serum-free medium for CHO cells protein-free (SAFC Bioscience) and Iscove's Modified Dulbecco's Medium, CD CHO medium.

Examples of cell culture medium also include optimised cell culture medium such as the ones described in WO2008/033517. These cell culture mediums are serum-free cell culture mediums comprising Part A, Part B, and Part C, wherein a) Part A consists essentially of a modified basal medium which excludes the following components; sodium bicarbonate, a buffer, mono-basic sodium phosphate, di-basic sodium phosphate, an osmolality regulator, a surfactant, and monosaccharide glucose;

b) Part B consists essentially of an inorganic iron source; and c) Part C comprises a recombinant growth factor; a buffer; an osmolarity regulator: an energy source; and at least two different non-animal hydrolysates.

Preferably, such serum-free culture mediums comprise:

a) a modified basal medium which excludes the following components sodium bicarbonate, buffer, mono-basic sodium phosphate, di-basic sodium phosphate, an osmolality regulator, a surfactant, and monosaccharide glucose;

b) about 8 to 12 ml/kg, or 122.45 mg/L ferric citrate; and c) about 4 to 8 mL/kg or 10 to 14 mg/kg recombinant human insulin; about 5 to 9 g/kg anhydrous glucose; about 0.5 to 0.7 g/kg L-glutamine; about 1 to 2 g/kg sodium bicarbonate; about 1 to 2 g/kg HEPES; about 2 to 3 g/kg NaCl; about 0.5 to 2 g/kg surfactant (Pluronic F-68); about 0.01 to 0.1 g/kg $NaH_2PO_4$—$H_2O$; about 0.4 to 0.5 g/kg $Na_2HPOWH_2O$; about 8 to 12 g/kg yeast-based hydrolysate; and about 60 to 70 g/kg plant-based hydrolysate.

In one embodiment of the invention, said cell culture medium comprising the haemoglobin as described above is intended for the culture of any type of cells, eukaryotes or prokaryotes, and cell lines. The cells to be cultured may be for example mammalian cells including human cells, fish cells, insect cells, mollusc cells, bacteria cells, annelids cells. . . . Example of type of cells to be cultured include, but are not limited to, kidney cells, hepatic cells, cardiac cells, pulmonary cells, intestinal cells, stomach cells, colon cells, pancreatic cells.

In one embodiment, the cell culture medium of the invention is optimized for the growth and/or protein production of CHO (Chinese Hamster Ovary cell) or Sp2/0 or PTG2b cells which express a protein of interest such as an antibody.

In another embodiment of the invention, said cell culture medium comprises the haemoglobin as described here above in a concentration of the haemoglobin is at least 0.05 g/l.

In one embodiment of the invention, said culture medium comprises the haemoglobin of the invention in a concentration of at least 0.250 g/l.

In another embodiment of the invention, said culture medium comprises the haemoglobin of the invention in a concentration of at least 1 g/l.

The person skilled in the art will be able to determine the concentration of haemoglobin to be added to a particular culture medium, in function of the physiological type of the cells to be cultured.

The cell culture medium may be present in any container, such as a bottle, a flask, a bag . . . .

The inventors also found that the haemoglobin of the invention in preservation solution is capable to maintain cell viability and cell metabolic activity, thus protecting the cells from cellular lesions induced by standard conservation.

Another object of the invention is a preservation solution that comprises the haemoglobin as described above. Said preservation solution presents the advantage of protecting cells from cellular lesions induced by standard conservation.

According to the invention, the term "preservation or maintenance solution" refers to any solution that can protect organs, tissues or cells from deleterious effects of ischemia reperfusion while maintaining metabolic needs of said organs, tissues or cells.

Conventional preservation solutions are aqueous solutions comprising electrolytes such as potassium, sodium, magnesium, calcium, chloride, sulphate and optionally impermeants such as mannitol, raffinose, saccharose, glucose, fructose, lactobionic acid, or gluconic acid, or optionally colloids such as albumin, hydroxyethyl starch, polyethylene glycol or dextran 40.

In one embodiment, said preservation solution comprises at least cations and aminoacids.

In one embodiment, said preservation solution comprises at least a disaccharide salt, a trisaccharide, a nucleoside, a tripeptide, a xanthine oxydase inhibitor and a starch derivative.

In one embodiment, said preservation solution comprises at least cations, aminoacids and a polyol.

Conventional preservation solutions include, but are not limited to, UW (Viaspan®), IGL1®, Celsior®, SCOT Maco, BMPS Belzer®, Custodiol® or Plegisol®. Preferably, the preservation solution of the invention comprises the haemoglobin as described above in Viaspan®.

Viaspan® is a commercial solution also known as University of Wisconsin solution (UW solution). It comprises potassium lactobionate (100 mM), $KH_2PO_4$ (25 mM), $MgSO_4$ (5 mM), raffinose (30 mM), adenosine (5 mM), glutathione (3 mM), allopurinol (1 mM) and hydroxyethyl starch (50 g/L).

Custodiol® is a commercial solution comprising sodium (15 mM), potassium (10 mM), magnesium (4 mM), calcium (0.015 mM), ketoglutarate/glutamic acid (1 mM), histidine (198 mM), mannitol (30 mM) and tryptophan (2 mM); it has an osmolarity of 310 mOsm/L.

The preservation solution may be present in any container, such as a bottle, a flask, a bag . . . .

In one embodiment of the invention, said preservation solution comprises haemoglobin as described above in a concentration of at least 0.005 g/l.

In another embodiment of the invention, said preservation solution comprises haemoglobin as described above in a concentration of at least 0.150 g/l.

In another embodiment of the invention, said preservation solution comprises haemoglobin as described above in a concentration from 0.150 g/l to 5 g/l.

The person skilled in the art will be able to determine the concentration of haemoglobin to be added to a preservation solution, in function of the organ or tissue or cells to be preserved.

In one embodiment of the invention, the temperature of said preservation solution can be from 2° C. to 40° C., preferably 4° C. to 37° C.

The preservation or maintenance solution according to the invention is capable of protecting
- living tissues, such as skin, corneas, organs, such as, for example, heart, lung, kidney, liver or pancreas,
- organ parts, such as, for example, muscles, pancreatic islets, heart valves, and the like, and
- tissues or organs cells.

Such protection includes protection from damage caused by ischemia and/or anoxia during storage prior to transplantation in a subject.

For organ preservation, the organ (e.g. kidney) is removed from a donor (living, encephalic death or non-heart beating) and immediately thereafter infused with the maintenance solution. In the case of removal following death, the organ should be removed as soon as possible to prevent ischemic damage, generally within about 30 minutes to about 90 minutes. The organ is stored in excess maintenance solution at a temperature in the range of from about 2° C. to about 12° C. (hypothermic perfusion) preferably 4° C. (cold ischemia) or in normothermic perfusion until later transplantation in a patient. Developments in the field of ex vivo organ preservation have advanced during the past quarter century to the point where organs for transplantation can be safely stored for variable periods depending upon the nature of the organ. Kidneys can be stored during one to two days (24-35 hours), livers and pancreases can be stored during less than one day (10-16/18 hours), but the clinically accepted limits for hearts is currently only about 6 hours or less. The present maintenance solution provides protection of various organs for at least the maximum allowable storage time for each organ. Organs can be conserved in static or pulsative modes. In static mode the organ is bathed in preservation solution and in pulsative mode the organ is perfused using a machine comprising a pump system.

In addition to preservation of individual tissues or organs, the preservation solution of the invention may also be used for whole body preservation of living donors, cadavers, including brain-dead individuals. In this manner preservation of the individual organs and other tissues for up to 8 hours or more can be achieved. The cadaver may be treated in substantially the same manner as described herein for bloodless hypothermic surgery, except that after the introduction of the maintenance solution at hypothermic temperature the individual is maintained under hypothermic temperature until such time as one or more organs are needed and are then harvested for use. The removed organs are then stored for transportation in additional fresh maintenance solution as needed.

The preservation solution of the invention may also be used to preserve and protect tissues, e.g., skin, from storage damage and possibly from the harmful effects of toxins and chemical toxicants. Thus, the preservation solution is also applicable to the storage of tissues, such as skin and corneas, for example, for later transplantation on, for example, burn patients, as well as to the protection of human skin against the harmful effects of toxins and toxicants, such as may be present in polluted environments, against chemical or germ warfare, and the like. For preservation of skin and corneal tissue for later transplantation, the tissue is removed from the donor and stored in maintenance solution for at least one week and up to about 2 to 4 weeks at 4° C. until transplantation.

The invention also provides a method for preserving organs or tissues or cells from said organs or tissues, comprising:
- washing said organs or tissues or said cells from said organs or tissues after their collection, with the preservation solution of the invention at a temperature from about 4° C. to 37° C., preferably from about 4° C. to 25° C., more preferably from about 4° C. to 15° C.,
- preserving said organs or tissues or said cells from said organs or tissues in static mode or dynamic perfusion at a temperature from about 4° C. to 37° C., preferably from about 4° C. to 25° C. and more preferably from about 4° C. to 15° C. in the preservation solution of the invention. The duration of the preservation will depend on the type of organs or tissues or cells as mentioned here above.

In one embodiment of the invention wherein the organs or tissues or cells are collected from a living or brain-dead subject, said organs or tissues or cells are washed and preserved preferably at 4° C.

In another embodiment of the invention wherein the organs or tissues or cells are collected from a subject who died from a cardiac arrest, said organs or tissues or cells are washed and preserved preferably at room temperature.

The inventors also found that the haemoglobin of the invention is stable in plasma and is particularly resistant to auto-oxidation.

One of the universal problems among red blood cells substitutes is their short life time as the plasma residence times for haemoglobin based oxygen carriers range from about 12 h for cross-linked haemoglobin to about 2 days for PEG-haemoglobin, compared to a mean residence time of 120 days for red blood cells. Acellular haemoglobins are particularly susceptible to oxidation and denaturation. Oxidised acellular haemoglobin can undergo further degradation through hemichrome formation, leading to release heme-iron and globin chain precipitation, which has the potential to cause endothelial and surrounding tissue damage.

It has been generally accepted that haemoglobin-based oxygen carrier should have properties resembling those of human blood. Correlating with this idea, the currently stage III haemoglobin-based oxygen carrier hemoglobin glutamer-250 (bovine) (hemoglobin-based oxygen carrier-201 [HBOC-201], Hemopure®; Biopure Corporation, Cambridge, Mass.) is glutaraldehyde-polymerized, bovine hemoglobin in a balanced electrolyte solution, has a $P_{50}$ between 36 and 38 mm Hg, which is similar to the P50 of the haemoglobin of the invention.

Another object of the invention is thus an artificial oxygen carrier for transfusion comprising the haemoglobin as above described.

As used herein, the term "artificial oxygen carrier for transfusion" refers to a biological product capable of replacing the haemoglobin present in the red blood corpuscles and capable of performing its function as a transporter of gas (oxygen and carbon dioxide). This artificial oxygen carrier for transfusion also has to supply oxygen to the tissues, where it becomes charged with CO2, to release this gas at the exchange surfaces (lungs). This artificial oxygen carrier for transfusion may also be called blood substitute.

The artificial oxygen carrier for transfusion of the invention presents the following advantages: it is not toxic, it has no pathogenic agent, it keeps for at least 6 weeks at 4° C. without oxidation, it is transfusable into all blood types, it has a sufficiently long residence time to ensure regeneration into natural haemoglobin of the organism into which it is transfused and it is eliminated by the organism into which it is transfused.

The expression "non-toxic" means that the artificial oxygen carrier for transfusion does not cause any pathological disorder of an immune-reaction, allergic or nephrotoxic type. The expression "has no pathogenic agent" refers to the absence of identified microorganisms or viruses. The absence of pathological disorders indirectly implies the absence of pathogens. The expression "keeps for at least 6 weeks at 4° C. without oxidation" means that the active site and in particular the iron present in the haem, which is involved in the oxygen bond remains in the form Fe2+ form (functional state). The oxidation of the active site is due to the passage of Fe2+—Fe3+ which is consequently not able anymore to bind oxygen. The expression "transfusable into all blood types" refers to the absence of blood typing (ABO or rhesus system). This haemoglobin could be considered as an universal haemoglobin since it is not a glycosilated molecule. The expression "has a sufficiently long residence time to ensure regeneration into natural haemoglobin of the organism into which it is transfused" refers to the presence of this haemoglobin in the blood system after at least 48 hours prior to transfusion. This time is long enough to enable an organism to synthesise back its own red blood cells. By way of illustration, within the framework of the transfusion of a human being, the time must advantageously be of the order of 48 hours. The expression "eliminated by the organism into which it is transfused without side effects" means that this extracellular haemoglobin seems to be eliminated by natural means not giving rise to any particular pathological disorder. In vertebrates, the life of a red blood cell lasts approximately 120 days. The red cell is then phagocyted (physiological haemolysis). The haemoglobin is then transformed into biliverdin and bilirubin which are eliminated by the bile. None of the side effects likely to be encountered with products of the prior art, in particular oedemas, problems of immunogenicity and nephrotoxicity do not exist within the framework of the present invention.

According to an embodiment, the artificial oxygen carrier for transfusion of the invention further comprises a pharmaceutically-acceptable aqueous solution.

Preferably, the artificial oxygen carrier for transfusion according to the invention includes haemoglobin as above described and artificial plasma. As used herein, artificial plasma refers to an injectable physiologic liquid, such as a plasma expander or a plasma substitute. An example of artificial plasma includes, but is not limited to, Hextend® (BioTime, Inc., Berkeley, Calif.).

Advantageously, the artificial oxygen carrier for transfusion of the invention is pyrogen-free and microbe-free.

This invention also relates to a blood pouch comprising an artificial oxygen carrier for transfusion according to the invention. Preferably, the blood pouch is an oxygen barrier film primary package (or about 0.155 cc per 100 square centimetres) per 24 hours per atmosphere at about 25° C. and an external relative humidity of about 50%, within which the artificial oxygen carrier for transfusion is sealed, thereby preserving the artificial oxygen carrier for transfusion in an environment that is substantially free of oxygen.

BRIEF DESCRIPTION OF THE FIGURES

The file of this patent contains at least one drawing executed in color. Copies of this patent with color drawings will be provided by the Patent and Trademark Office upon request and payment of the necessary fee.

EXAMPLES

Figure 1:
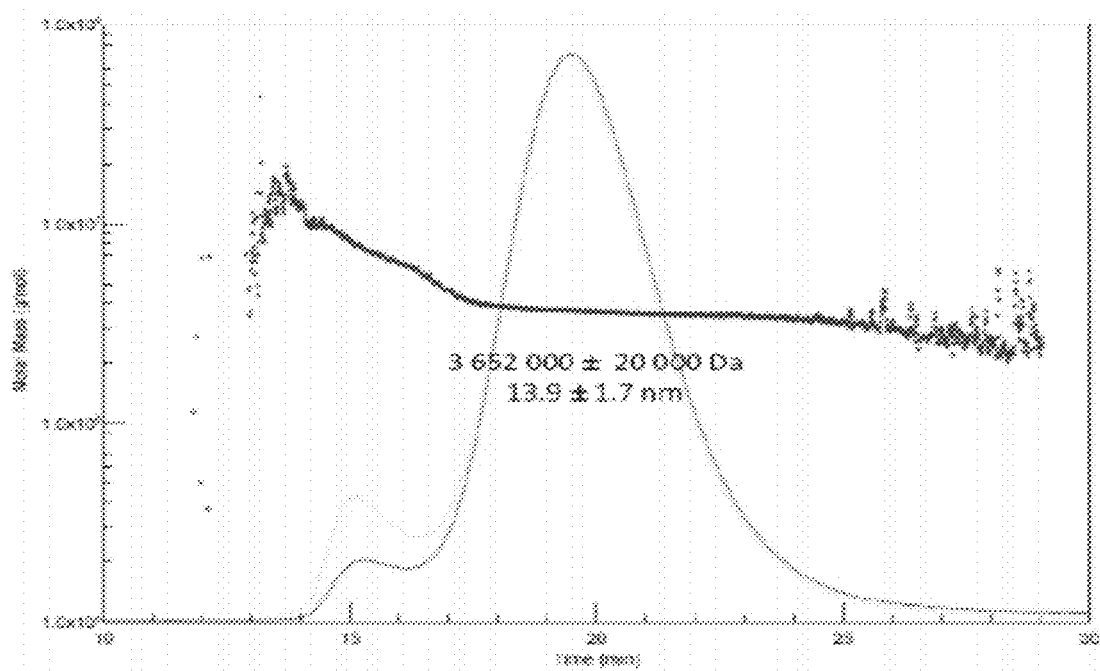
FIG. 1: Structural analysis of *Nereis* Haemoglobin

Extraction and Purification of *Nereis* Haemoglobin Samples

The *Nereis* species were obtained by a marine stockbreeder who farms these worms for shrimp and fish aquaculture. Living ragworms were bled.

The blood samples are collected on ice. After cold centrifugation (15 000 g for 15 min at 4° C.) to eliminate any tissue debris, the supernatants are frozen at −20° C. or in liquid nitrogen, or immediately purified.

Purification of the Haemoglobins

Before purification, the thawed sample is centrifuged, at 5 000 g for 5 mM at 4° C. After centrifugation, a small residue is generally present; this is eliminated. The supernatant is purified by Low pressure filtration using a 2.5*100 cm Sephacryl S-400 HR column (GE Healthcare, separation range between $2 \times 10^4$-$8 \times 10^6$ kDa). The samples are eluted with the storage buffer as described here above (150 mM NaCl, 2 mM CaCl2, 1.5 mM CaCl2, 5 mM KCl, 50 mM Hepes, pH 7.2). The rate used is generally 0.4 to 0.5 ml/min. The absorbance of the eluate is followed at two wave lengths: 280 nm (protein absorbance peak) and 414 nm (haemoglobin absorbance peak). The fractions containing the haem are concentrated using Centricon-100 (15 ml) tubes or using an agitation cell retaining the molecules with a weight above or equal to 10 000 Da. Two purification processes following the same protocol might be necessary to obtain pure fractions. The purified sample is filtrated on 0.2 µm before storage at −80° C.

The concentration of haemoglobin obtained was about 50 mg/ml and the purity of the haemoglobin was 95%.

The samples were kept either frozen or under liquid nitrogen until use.

Gel Filtration LC Analysis

Analytical gel filtration was performed on 5 to 200 µl of injected sample on a 1×30 cm Superose 6-C (fractionation range from 5 to 5000 kDa, GE Healthcare) using a high-pressure HPLC system (Waters, milford, MA, USA). The elution buffer is 0.1N Tris-HCl buffer at pH 7.2. The elution (flow rate: 0.5 ml/min) was monitored with a photodiod array detector (Waters 2996) over the range 250-700 nm Chromatographic data were collected and processed by the Empower software (Waters). The percentages of each subunit were determined by integrating the chromatogram at 414 nm (characteristic of heme) and 280 nm (characteristic of protein) with the Empower software.

Multi-Angle-Laser-Light-Scattering

The molecular weight and the gyration radius of the native haemoglobin were determined with MALLS detector (DAWN EOS system, Wyatt Technology Corp., Santa Barbara, Calif., USA) directly on-line with the HPLC system and the Superose 6 column Chromatographic data were collected and processed by the Astra software (Wyatt Technology Corp.). The Zimm fit method was used for molecular mass determinations. In this method, the concentration dependence of the refractive index was set to 0.19 ml g$^{-1}$ (typical for human haemoglobin). The sample was kept at 4° C. until the elution which was performed at room temperature.

Mass Spectrometry Analysis

Electrospray data were acquired on an ESI-Q-TOF (Q-TOF II; Micromass, Altrincham, UK) mass spectrometer scanning over the mass-to-charge ratio (m/z) range 600-2500 in 10 s/scan. Data were accumulated over 3 mM to produce the final spectrum. The cone voltage (counter electrode to skimmer voltage) was set to 60 V. A 200-µl solution of purified, native Hb was desalted four times against 4 ml MilliQ water (at 4° C.) using centrifugal filters with a molecular weight cut-off of 100 kDa (Amicon Ultra-4, Millipore). ESI-MS analyses were performed on the non-reduced Hb, the reduced Hb, and on the reduced and carbamidomethylated Hb to determine the association of subunits into dissulfide-bridged structures. Samples with a protein concentration of 0.5 µg µl$^{-1}$ in 1:1 (v/v) acetonitrile/water containing 0.2% (v/v) formic acid were introduced into the electrospray source at 5 µl min$^{-1}$ Hb (0.9 mg ml$^{-1}$) was reduced with 10 mM DTT at room temperature under alkaline conditions in the presence of 100 mM ammonium bicarbonate. After 10 min incubation, a 10-µl aliquot was mixed with 40 µl MilliQ and 50 µl acetonitrile containing 0.2% formic acid and analysed by ESI-MS. After 20 min incubation under reducing conditions, Hb (0.7 mg ml$^{-1}$) was carbamidomethylated with 4 mM iodoacetamid at room temperature for 10 mM and 10 hours, respectively, after which 12.75-µl aliquots were mixed with 37.75 µl MilliQ and 50 µl acetonitrile containing 0.2% formic acid and analysed by ESI-MS. Carbamidomethylation was carried out for total cystein determination. Mass scale calibration employed the multiply charged series from horse heart myoglobin (16951.7 Da; Sigma, St Louis, Mo.). The raw multicharged ESI-MS spectra were deconvoluted using maximum-entropy-based analysis supplied with the instrument. Molecular masses are based on the atomic weights of the elements given by IUPAC.

Oxygen Binding Properties

Oxygen equilibrium curves were determined on 3 µl samples using a thermostated diffusion chamber (Colmorgen et al. 1997 J. Comp. Physiol. 167B:309) linked to cascaded Wosthoff gas mixing pumps (Bochum, Germany). The diffusion chamber was placed in the light path of a spectrometer (Hitachi U1100) at 436 nm Oxygenation data based on at least three equilibrium steps between 0.2 and 0.8 fractional saturation (Y) were converted to Hill plots (log [Y/1−Y]) against log PO2, where PO2 is the oxygen partial pressure) for the estimation of the half-saturation oxygen partial pressure ($P_{50}$) and Hill's cooperativity coefficient at half-saturation ($n_{50}$).

Cell Culture Medium

Cell Lines and Cell Culture Conditions

CHO DXB11, a dihydrofolate reductase (dhfr-) Chinese Hamster Ovary cell line, SP2/0 and PTG2b cell lines were used. Both CHO and SP2/0 cells were seeded at 0.5*10$^5$ cells/ml in shake flasks containing serum-free medium, specifically designed for optimal suspension growth and protein production, supplemented with 8 mM L-Glutamine and different concentrations of the haemoglobin. Cells were grown in batch culture without refeeding at 37° C. in a shaking incubator at least for 1 day, preferably at least 4 days, preferably at least 8 days.

Sampling and Studied Parameters

Samples were removed at days 0, 1, 4, 6 and 8 post-seeding to determined cell count, cell viability and protein production. Cell count and cell viability were measured by the tryphan blue exclusion technique using a Vi-CELL™ Analyzer (Beckman Coulter). Total antibody production was measured using an ELISA assay specific for the IgG being expressed according to manufacturer's instructions (ELISA kit, Bethyl Laboratories).

Cell Preservation

Cell Line and Cell Culture Conditions

Experiments were carried out using an epithelial cell line originally derived from porcine kidneys: LLC-PK1.

LLC-PK1 cells were cultured in M199 medium supplemented with 3% SVF, 100 U/ml penicillin, 100 µg/ml streptomycin and 2 mM L-Glutamine.

LLC-PK1 cells were seeded in a 6 wells plate at a concentration of 1.6.10$^5$ cells/ml. After 48 h of culture, the cells were washed in PBS and maintained at 4° C. during 24 h in 1.2 ml of UW solution (Viaspan®) or Custodiol® solution alone or in the presence of different concentration of the haemoglobin.

Cell Viability Detection

LDH Test

Cell viability was determined by detection of lactate dehydrogenase (LDH) as the presence of this enzyme in the cells reflects permeabilization of the plasmic membrane and thus cell death.

After 24 h of conservation in the preservation solution, supernatant was eliminated and cells were washed 3 times in PBS and then lysed in 1.2 ml of PBS containing 0.1% of Triton X-100.

The quantity of LDH present in the cells was determined by a colorimetric dosage according to the manufacturer's instructions (TOX7, Sigma-Aldrich). The delta of absorbance measured at 490 nm and 630 nm is directly proportional to the quantity of enzyme present in the sample.

MTT Test

The MTT assay is another in vitro cell viability assay used to determine a reduction in cell viability. After 24 h of conservation in the preservation solution, supernatant was eliminated and cells were washed 2 times in PBS. The tetrazolium compound MTT (3-[4, 5-dimethylthiazol-2-yl]-2,5-diphenyltetrazolium bromide) was added to the wells at a concentration of 0.5 mg/ml in PBS and the cells were incubated 30 min at 37° C. MTT is reduced by metabolically active cells to insoluble purple formazan dye crystals. The crystals were solubilized by adding 2 ml of DMSO and the absorbance was detected with a spectrophotometer. The delta of absorbance measured at 535 nm and 690 nm is directly proportional to the metabolic activity of the cells.

Results

Structural Analysis

Molecular weight and gyration radius were determined by MALLS (FIG. 1).

Subunit and polypeptid chains composition determined by ESI-MS (Table 1).

TABLE 1

| | Subunits (non reduced conditions) | | | Polypeptide chains (reduced conditions) | | | |
|---|---|---|---|---|---|---|---|
| | Mw (Da) | Free Cys | name | Mw (Da) | Cys | name | Disulphide bridge |
| Monomeres | 15448.0 | 0 | an1 | | 0 | | |
| | 15885.0 | 0 | an2 | | 2 | | 1 intra- |
| Trimeres | 49372.5 | 0 | T1 | 16145.5 | 1 | an3 | 1 inter- |
| | | | | 16494.5 | 1 | an4 | 1 inter- |
| | | | | 16734.5 | 4 | an5 | 2 inter-<br>1 intra- |
| Linker | 50606.9 | | | | | | |

Functional Analysis

The functional properties of the *Nereis* haemoglobin were determined at 3 different temperatures: 4° C., 15° C. and 37° C. Results are shown in Table 2.

TABLE 2

| Temperature (° C.) mean | stdev | P50 (mmHg) | Hemoglobin stdev | n50 | stdev |
|---|---|---|---|---|---|
| 6.65 | 0.40 | 10.98 | 1.27 | 1.19 | 0.04 |
| 16.51 | 0.13 | 16.57 | 1.96 | 1.17 | 0.10 |
| 36.56 | 0.29 | 37.11 | 6.00 | 1.47 | 0.40 |

Stability of the *Nereis* Haemoglobin in Rat Plasma

The haemoglobin was diluted in rat plasma at a concentration of 1 mg/ml and maintained at 20° C. The solution is centrifuged at 10000 g for 2 min at 4° C. and then filtrated on a 0.45 µm filter before injection.

Figure 2:
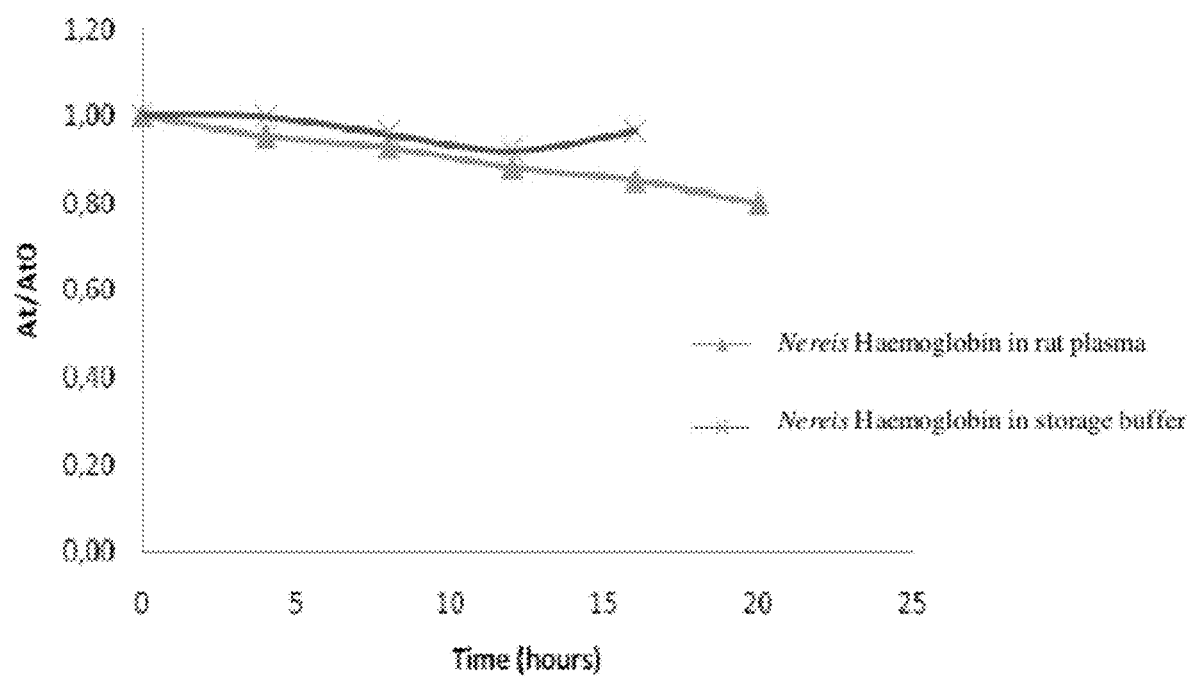
FIG. 2: Stability of *Nereis* Haemoglobin in rat plasma

FIG. 2 shows that *Nereis* haemoglobin is stable in rat plasma.

Effect of the *Nereis* Haemoglobin in Preservation Solution.

1—Analysis of LLC-PK1 Cells Viability by Detection of the Liberation of Lactate Dehydrogenase (LDH)

The results are expressed in percentage of LDH quantity detected in cells maintained at 4° C. in the preservation solution compared to LDH quantity detected in cells before cold preservation (T0). Different concentrations of haemoglobin: 0.039. 0.078. 0.156. 0.312. 0.625 and 1.25 g/l were added to the preservation solution.

The percentage of LDH liberation is calculated as following: 100−[(LDH cells)×100/(LDH cells at T0)].

Figure 3:
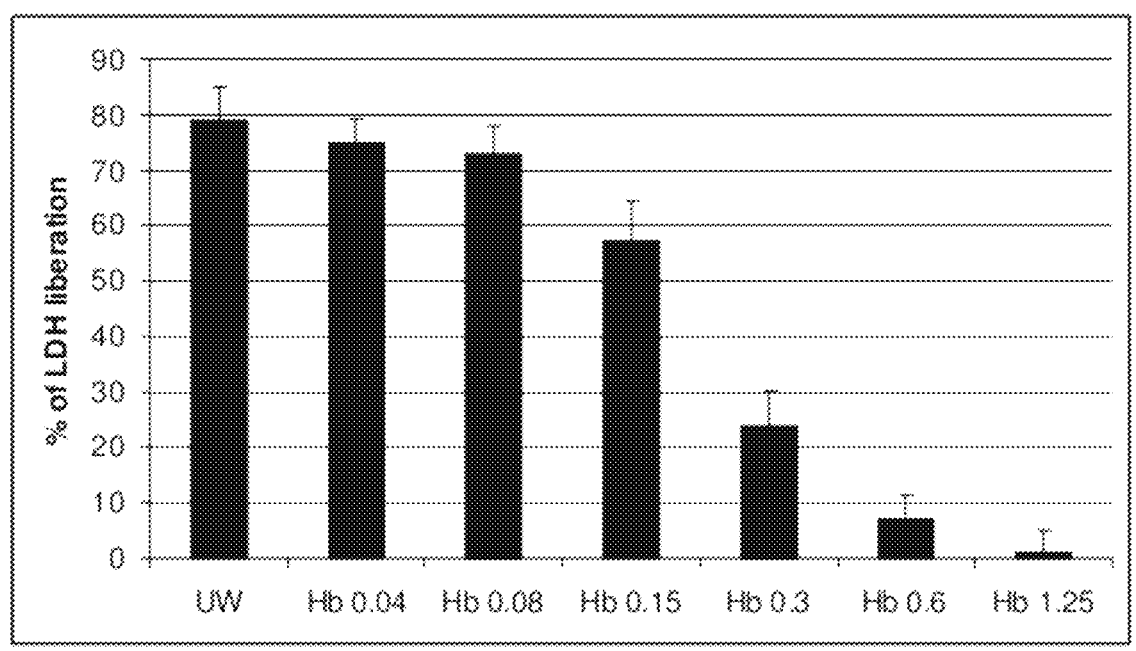
FIG. 3: Percentage of LDH liberation in function of *Nereis* Haemoglobin concentration

The results are shown in Table 3 and FIG. 3.

TABLE 3

| | UW | Hb 0.039 | Hb 0.078 | Hb 0.156 | Hb 0.312 | Hb 0.625 | Hb 1.25 |
|---|---|---|---|---|---|---|---|
| Mean | 79 | 75 | 73 | 57 | 24 | 7 | 2 |
| SD | 5.9 | 4.3 | 4.9 | 7.4 | 6.3 | 4.5 | 2.3 |

Conservation of LLC-PK1 cells at 4° C. during 24 h induces about 80% of cell death. The presence of *Nereis* haemoglobin in UW solution (Viaspan®) protects LLC-PK1 cells from cell death in a dose-dependent manner and this protection is almost complete at 0.625 g/l.

2—Analysis of LLC-PK1 Cells Metabolic Activity by MTT Test

The results are expressed in percentage of metabolic activity detected in cells maintained at 4° C. in the preservation solution compared to metabolic activity detected in cells before cold preservation (T0).

Different concentrations of haemoglobin: 0.04. 0.08. 0.156. 0.312. 0.625. 1.25 and 2.5 g/l were added to the preservation solution.

The percentage of metabolic activity is calculated as following: (metabolic activity of cells)/(metabolic activity of cells at T0)×100.

Figure 4:
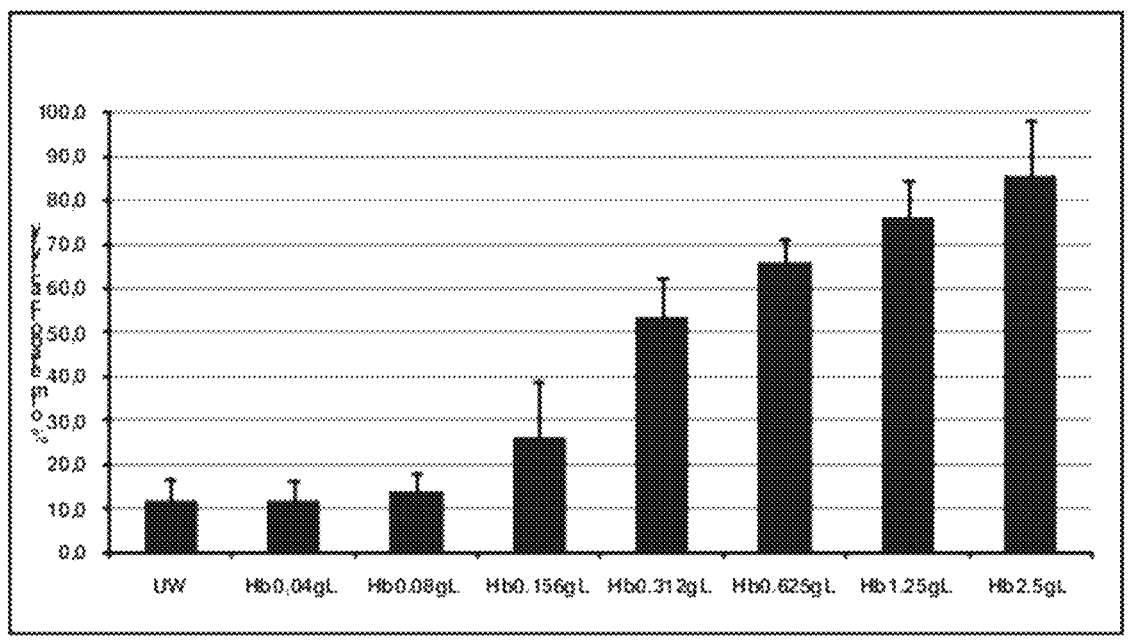
FIG. 4: Percentage of metabolic activity in function of *Nereis* Haemoglobin concentration

The results are shown in Table 4 and FIG. 4.

TABLE 4

| | UW | Hb 0.039 | Hb 0.078 | Hb 0.152 | Hb 0.312 | Hb .625 | Hb 1.25 | Hb 2.5 |
|---|---|---|---|---|---|---|---|---|
| Mean | 11.3 | 11.5 | 13.5 | 25.9 | 53.2 | 65.6 | 75.7 | 85.1 |
| SD | 5.3 | 5.1 | 4.8 | 13.2 | 9.1 | 5.8 | 8.6 | 12.8 |

Results show that the presence of haemoglobin in UW solution (Viaspan®), in particular at a concentration higher than 0.625 g/l, allows the preservation of the metabolic activity of LLC-PK1 cells. Same results were obtained with haemoglobin in Custodiol® solution (data not shown).

Effect of the *Nereis* Haemoglobin in Cell Culture Medium.

1—Stability of the Haemoglobin in Cell Culture Medium at 37° C.

The haemoglobin (1.25 mg/mL) was added to the following cell culture media: DMEM, CDCHO, ExCell, GR7F, a-MEM-SVF, a-MEM-PRP, SCIVAX media.

The absorbance between 250 and 700 nm was measured at different points of time.

Figure 5:
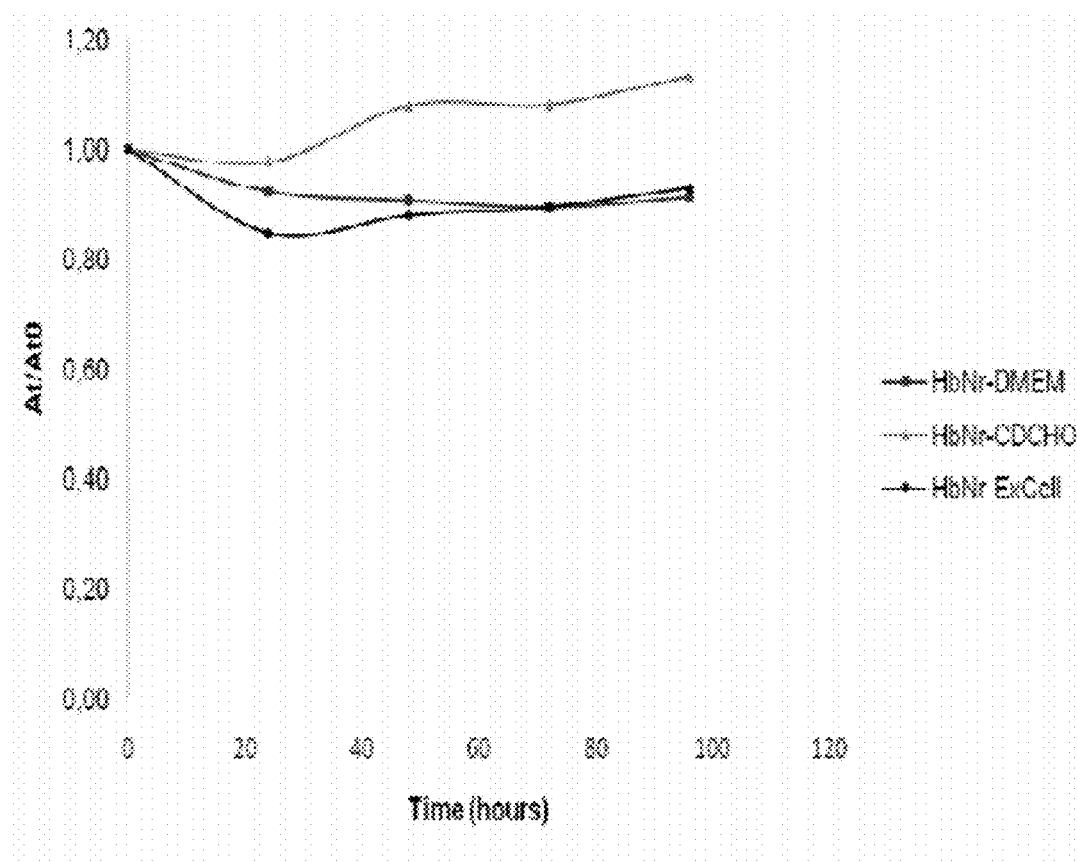
FIG. 5: Stability of *Nereis* Haemoglobin in cell culture medium at 37° C.

Table 5 and FIG. 5 show no dissociation of the haemoglobin during time, suggesting that the haemoglobin is stable during time in cell culture medium.

TABLE 5

| Time | DMEM At/At0 (414 nm) | CDCHO At/At0 (414 nm) | ExCell At/At0 (414 nm) |
|---|---|---|---|
| 0 | 1.00 | 1.00 | 1.00 |
| 24 | 0.92 | 1.00 | |
| 48 | 0.91 | 1.00 | 0.88 |
| 72 | 0.90 | 1.00 | 0.90 |
| 96 | 0.91 | 1.05 | 0.93 |
| 168 | 0.83 | 1.00 | 0.97 |
| 214 | 0.78 | 0.99 | |
| 334 | 0.70 | 0.78 | |
| 358 | | | 0.90 |
| 384 | 0.65 | 0.76 | 0.91 |

Figure 6:
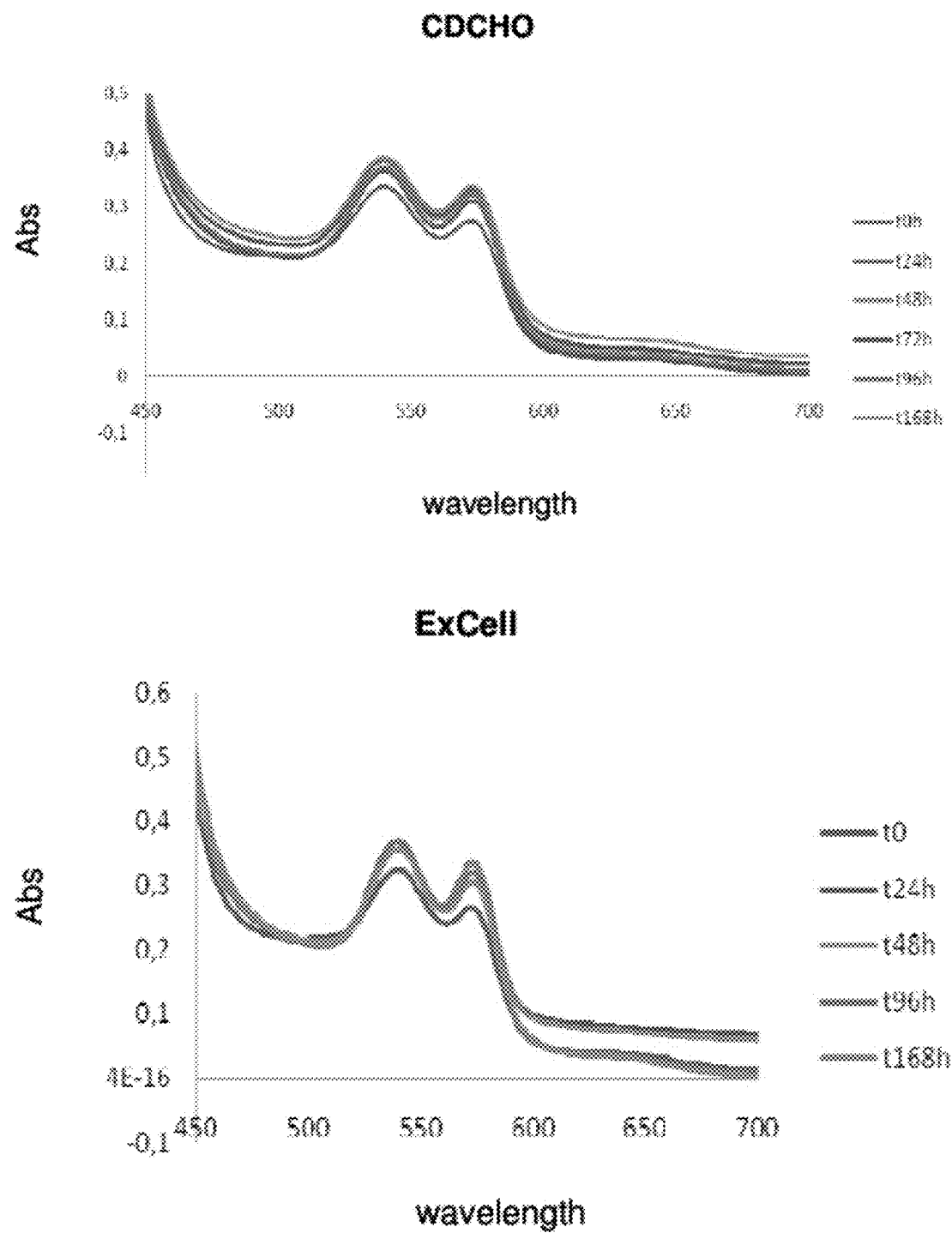
FIG. 6: Stability of *Nereis* Haemoglobin in cell culture medium at 37° C.

FIG. 6 shows that no oxidation occurs during time, suggesting that the haemoglobin is stable at 37° C. in cell culture medium during time.

In addition, no dissociation and no oxidation of the haemoglobin during time was observed when cultured in GR7F, a-MEM-SVF, a-MEM-PRP, and SCIVAX media (data not shown).

2—Effect of the Haemoglobin on Cell Viability, Cell Growth and Protein Production CHO and Sp2/0 cell lines were cultivated during 8 to 11 days in cell culture medium alone or in the presence of 0.05 g/l, 0.25 g/l and 1 g/l of the haemoglobin. PTG2b cell lines were cultivated during 7 days in cell culture medium alone or in the presence of 0.125 g/l, 0.25 g/l and 1 g/l of the haemoglobin.

CHO, SP2/0 and PTG2b cells were seeded at day 0 (D0) at a density of $0.5*10^5$ cells/ml. Cell count and cell viability were measured by the tryphan blue exclusion technique using a Vi-CELL™ Analyzer (Beckman Coulter). Total protein production was measured using an ELISA assay specific for the protein being expressed according to manufacturer's instructions (ELISA kit, Bethyl Laboratories).

Figure 7:
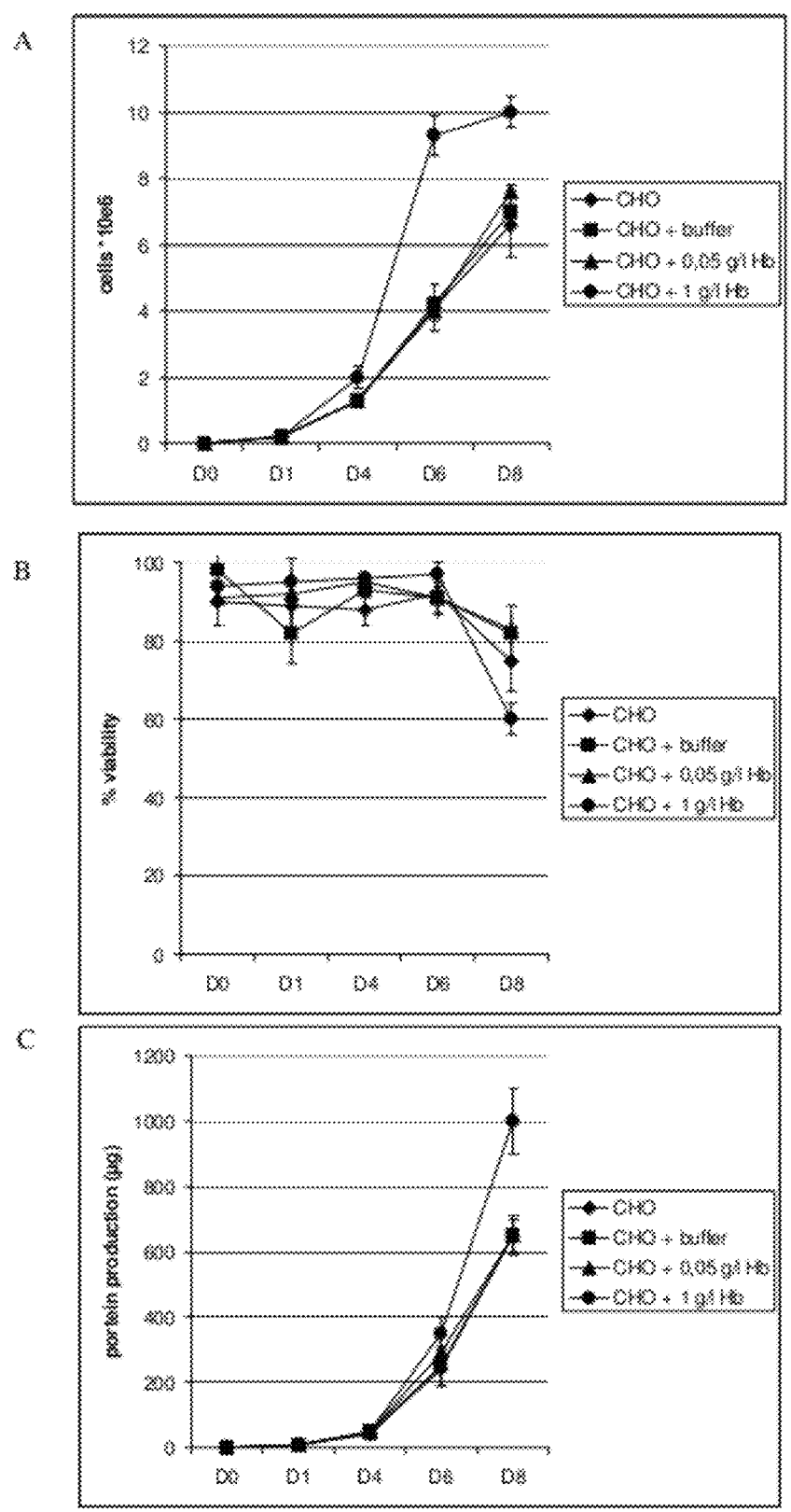
FIG. 7: Effect of *Nereis* Haemoglobin on CHO cells viability, growth and protein production

FIG. 7 shows that 1 g/l of haemoglobin enhances CHO cell growth (7A) and CHO antibody production (7C) while cell viability is maintained (7B).

Figure 8:
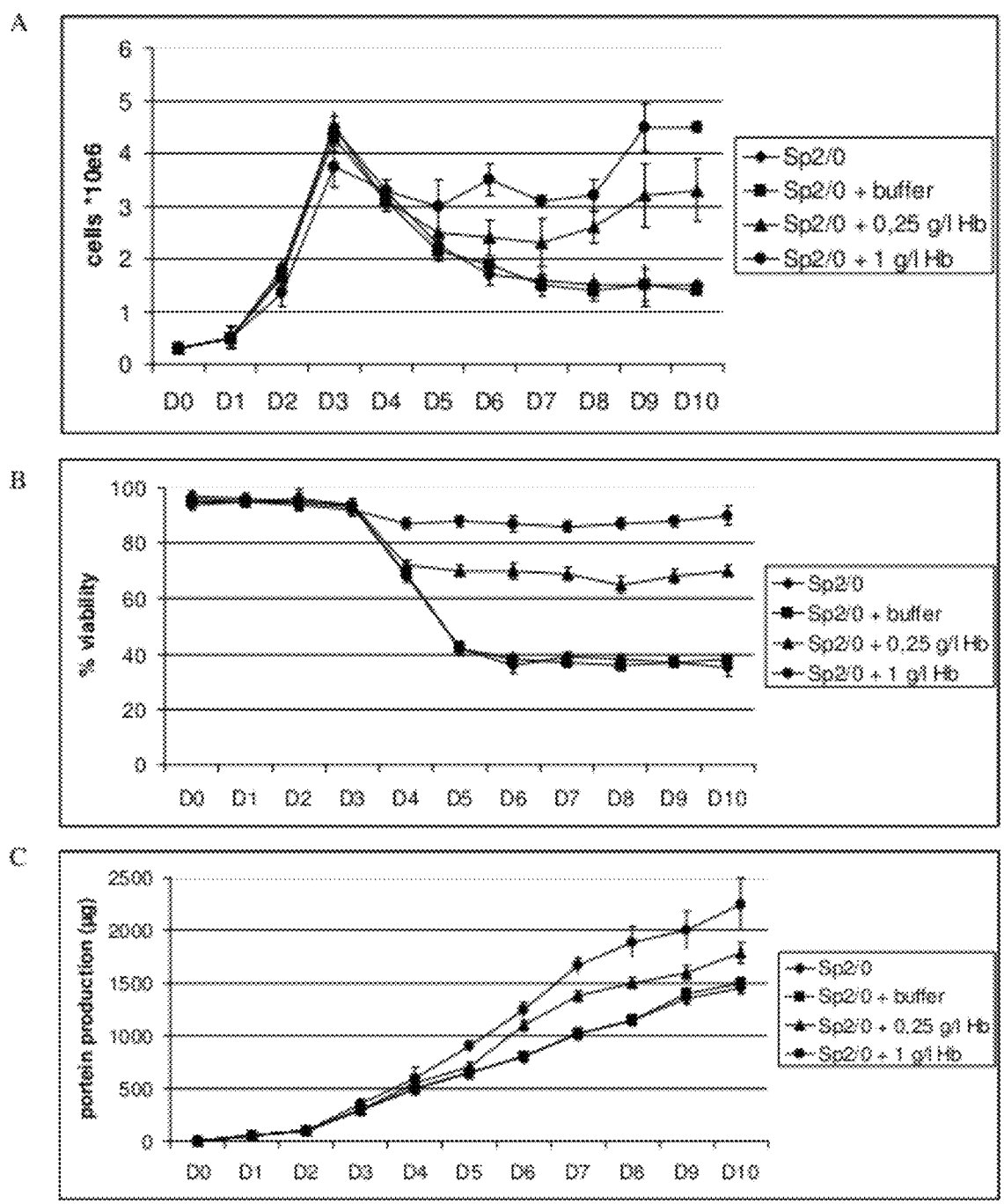
FIG. 8: Effect of *Nereis* Haemoglobin on Sp2/0 cells viability, growth and protein production

FIG. 8 shows that the presence of haemoglobin enhances in a dose-dependent manner Sp2/0 cell growth (8A) and viability (8B) and Sp2/0 antibody production (8C).

Figure 9:
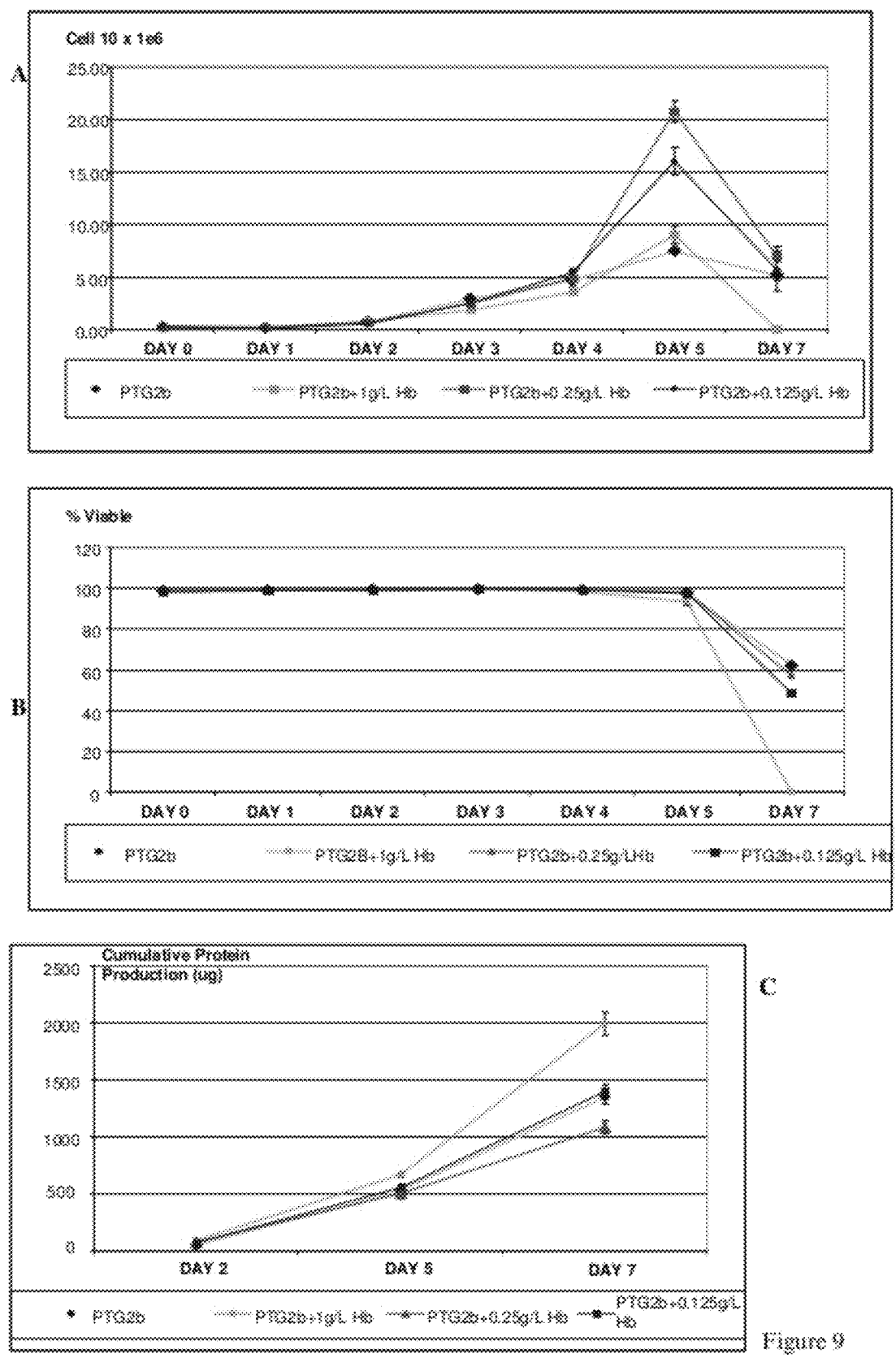
FIG. 9: Effect of *Nereis* Haemoglobin on PTG2b cells viability, growth and protein production

FIG. 9 shows that the presence of haemoglobin maintains PTG2b cell growth (9A) and viability (9B) and enhances PTG2b antibody production (9C).

The invention claimed is:

1. A composition for in vitro cell culture, comprising:
   A) a serum-free nutritive cell culture medium solution for the maintenance, growth, propagation, and/or expansion of cells in an artificial environment outside of a multicellular organism or tissue,
   B) a purified and function hemoglobin isolated from *Nereis virens*, wherein said hemoglobin has no free cysteine and no glycosylations,
   said hemoglobin having:
      (i) a $P_{50}$ from 5 to 15 mm Hg at 6-7° C.,
      (ii) a $P_{50}$ from 12 to 20 mm Hg at 16-17° C., and
      (iii) a $P_{50}$ from 20 to 50 mm Hg at 36-37° C.,
   C) a buffer,
   D) isolated cells which grow and produce a recombinant protein, and
   wherein components A), B), C), and D) are in mixture in the cell culture medium solution, and
   wherein of the hemoglobin has a concentration of at least 0.050 g/l.

2. The composition according to claim 1, wherein the concentration of the hemoglobin is at least 1 g/l.

3. The composition according to claim 1, wherein said hemoglobin has:
   (i) a $P_{50}$ from 9 to 12 mm Hg at 6-7° C.,
   (ii) a $P_{50}$ from 15 to 18 mm Hg at 16-17° C., and
   (iii) a $P_{50}$ from 30 to 44 mm Hg at 36-37° C.

4. The composition according to claim 1, wherein said hemoglobin has a molecular weight of from 3 to 4 million Daltons.

5. The composition according to claim 1, wherein the buffer further comprises $CaCl_2$, NaCl, $MgCl_2$, and KCl.

6. The composition according to claim 5, wherein the composition has a pH of 7.0 to 7.8.

7. The composition according to claim 1, wherein said cell culture medium solution comprises a medium selected from the group consisting of Dulbecco's Modified Eagle's Medium (DMEM), DMEM/F12, Minimal Essential Medium (MEM), Basal Medium Eagle (BME), RPMI 1640, F-10, F-12, alpha-Minimal Essential Medium (alpha-MEM), Glasgow's Minimal Essential Medium (G-MEM), Iscove's Modified Dulbecco's Medium, and CD-CHO medium.

8. The composition according to claim 1, wherein said cell culture medium solution comprises:
   a) a basal medium;
   b) ferric citrate;
   c) insulin, glucose, L-glutamine, sodium bicarbonate, HEPES, NaCl, surfactant, $NaH_2PO_4$—$H_2O$, yeast-based hydrolysate, and plant based hydrolysate.

9. The composition according to claim 1, wherein the composition is in the form of an aqueous solution, a frozen solution, or a thawed solution.

10. The composition according to claim 1, wherein the concentration of the hemoglobin is 0.250 to 200 mg/ml.

11. The composition according to claim 8, wherein the concentration of the hemoglobin is at least 0.250 g/l.

12. The composition according to claim 1, wherein the buffer comprises at least one of HEPES and Tris, wherein the cell culture medium solution has a pH of 6.0 to 7.8.

13. The composition according to claim 1, wherein the cell culture medium solution has a pH of 6.0 to 7.8.

14. The composition according to claim 1, wherein the concentration of the hemoglobin is 0.250 to 1.25 mg/ml.

15. The composition according to claim 1, wherein the isolated cells are eukaryotes or prokaryotes, which produce an antibody.

* * * * *